United States Patent [19]

Fullerton

[11] 4,292,041

[45] Sep. 29, 1981

[54] SURFACTANT ASSAY

[75] Inventor: W. Wardle Fullerton, King of Prussia, Pa.

[73] Assignee: Merck & Co., Inc., Rahway, N.J.

[21] Appl. No.: 90,768

[22] Filed: Nov. 2, 1979

[51] Int. Cl.³ ............................................. G01N 31/08
[52] U.S. Cl. .............................. 23/230.3; 23/230 R; 23/902; 210/658
[58] Field of Search .................... 23/230 R, 230.3; 210/31 C, 658

[56] References Cited

U.S. PATENT DOCUMENTS 4,064,041 12/1977 Halpaap .......................... 210/31 C
4,129,560 12/1978 Zoltobrocki ..................... 210/31 C

OTHER PUBLICATIONS

J. R. Bodenmiller et al., Anal. Chem., 44(6), 926 (1972).
K. Hayashi, Anal. Biochem., 67, 503–506 (1975).
M. J. Rosen, "Systematic Analysis of Surface—Active Agents", 2nd. Edition, 60, 61, 65, 66, 68, 71–76, Wiley–Interscience, New York, 1972.
"Thin–Layer Chromatography", E. Stahl, ed., 493, 498, 499, Academic Press, New York, 1965.
S. Goldstein et al., Anal. Biochem., 64, 130–135 (1975).
P. W. Holloway, Anal. Biochem., 53, 301–308 (1973).
K. Simons et al., J. Mol. Biol., 80, 119–133 (1973).
Kedar et al., Israel J. Med. Sci., 9 (3), 268 (1973).

*Primary Examiner*—Sidney Marantz
*Attorney, Agent, or Firm*—Donald J. Perrella; Hesna J. Pfeiffer

[57] ABSTRACT

Thin layer chromatography is used to separate various surfactants. The support medium is silica gel on a glass or acrylamide plate. The developing solvent is chloroform/methanol/water. After drying, the surfactants are detected at extremely low levels with iodine vapor, rhodamine 6G in methanol or phosphomolybdic acid in ethanol/ether, or radiolabelled surfactant. A method is given for the separation of surfactants from proteins or glycoproteins or lipoproteins or polysaccharides, or lipopolysaccharides.

10 Claims, No Drawings

SURFACTANT ASSAY

BACKGROUND OF THE INVENTION

It is a common expedient in membrane chemistry to extract proteins, glycoproteins, lipoproteins, polysaccharides or lipopolysaccharides from membranes or organisms by treatment with a surfactant. No satisfactory methods have been available heretofore, however, for the detection, quantitation and separation of the extracting surfactants from the proteins or polysaccharides, particularly extremely low levels of surfactants. Most of the prior art procedures are spectrophotometric. Most of them lack sensitivity below 5 $\mu$g and most of them can give false results due to interference by lipids, other type surfactants and proteins. None of them is applicable to all of the surfactants commonly used in membrane chemistry, i.e., one uses a different procedure with each surfactant.

OBJECTS OF THE INVENTION

It is an object of the present invention to provide a more sensitive method for detecting and quantitating surfactants, particularly extremely low levels of surfactants. Another object is to provide an improved method for separating extremely low levels of surfactants from proteins or polysaccharides. These and other objects of the present invention will be apparent from the following description.

SUMMARY OF THE INVENTION

The detection, quantitation and separation of surfactants, particularly extremely low levels of surfactants, i.e., less than 1 $\mu$g, from proteins, glycoproteins, polysaccharides, lipopolysaccharides or lipoproteins is accomplished with improved sensitivity and effectiveness. Thin layer chromatography is used to separate various surfactants. The support medium is silica gel or alumina gel on a suitable support such as, for example, a glass or acrylamide plate. The developing solvent is preferably chloroform/methanol/water. After drying, the surfactants are detected at extremely low levels with iodine vapor, rhodamine 6G in methanol, phosphomolybdic acid in ethanol/ether or by using radiolabeled surfactant.

DETAILED DESCRIPTION

The present invention relates to the detection quantitation and separation of surfactants and, more particularly, to the detection, quantitation and separation of surfactants in membrane chemistry.

It is known that one can extract proteins, glycoproteins, lipoproteins, polysaccharides or lipopolysaccharides from membranes of organisms by treatment with a surfactant. As examples of some frequently used surfactants there may be mentioned nonionic surfactants such as polyoxyethylene octyl phenol (Triton X-100); alkylphenoxypolyethoxy (3) ethanol, polyoxyethylene (20) sorbitan monolaurate (Tween 20), polyoxyethylene (20) sorbitan monopalmitate (Tween 40), polyoxyethylene (20) sorbitan monostearate (Tween 60), polyoxyethylene (20) sorbitan tristearate (Tween 65), polyoxyethylene (20) sorbitan monooleate (Tween 80), polyoxyethylene (20) sorbitan trioleate (Tween 85), polyoxyethylene (20) palmitate (G2079), polyoxyethylene (4) lauryl ether (Brij 30), polyoxyethylene (20) lauryl ether; polyoxyethylene (23) lauryl ether (Brij 35), polyoxyethylene (20) cetyl ether (Brij 58), polyoxyethylene (20) stearyl ether (Brij 78), polyoxyethylene (20) oleyl ether (Brij 92), polyoxyethylene (25) hydrogenated castor oil (G1292), polyoxyethylene (25) oxypropylene monostearate (G2162), anionic surfactants such as sodium dodecyl sulfate, sodium cholate, sodium deoxycholate, and sodium taurocholate, and cationic surfactants such as hexadecyltrimethyl ammonium bromide (Cetavlon), cetyltrimethyl ammonium bromide, and N-hexadecylpyridinium chloride. A satisfactory method to detect, quantify and separate a surfactant, particularly in low concentration, from the membrane extract, however, is unavailable. The prior art methods are usually spectrophotometric.

According to the present invention the surfactant or surfactant-containing material is extracted with a solvent mixture containing one or more organic solvents and water. Typically the organic solvents comprise a haloalkane and a water-miscible alkanol. A prefered solvent mixture is chloroform, methanol and water. The extraction may take place over a period of from about 30 minutes to about 3 hours at a temperature of from about 10° to about 40° C.

The developing solvent is a mixture of solvents which solubilizes the detergent and distributes the detergent over the middle portion of the chromatographic plate. The solvent generally contains one or more organic solvents and water. A preferred solvent system comprises chloroform, methanol and water. The chromatography may take from about 30 minutes to about 3 hours at temperatures of from about 10° to about 40° C.

The following example illustrates the present invention without, however, limiting the same thereto.

EXAMPLE 1

*N. gonorrhoeae* cells are streaked on agar and incubated 18 hours in 150 mm diameter Petri dishes at 37° C. in the presence of 5% $CO_2$. The cells are harvested by scraping with a Dacron tip swab using 10 ml of pyrogen free saline per 5 dishes. Each 10 ml of cell suspension is transferred immediately to a sterile centrifuge tube, and chilled on ice. The chilled cell suspensions are centrifuged at 5,000$\times$g for 20 minutes and the supernatant liquids decanted. To each pellet is added 1.0 ml of 5% Triton X-100, 0.01 M Tris (hydroxymethyl)aminomethane, 0.01 M $MgCl_2$, pH 8.5. Each pellet is extracted for 30 minutes at 19°–23° C. with stirring and then centrifuged for 1 hour at 100,000 $\times$g. The supernatant liquids are decanted. The uncontaminated pellets are pooled, suspended in 20 ml physiological saline followed by the addition of 80 ml of absolute ethanol, and transferred to 150 ml Sorvall centrifuge tubes. The suspension is mixed thoroughly, allowed to stand at $-20°$ C. for 24–72 hours and centrifuged for 20 minutes at 5,000$\times$g. The supernatant liquid is discarded. The pellet is washed in 80% ethanol, resuspended in sterile, pyrogen-free deionized water and freeze-dried.

The freeze-dried preparation containing proteins, glycoproteins, polysaccharides, lipopolysaccharides or lipoproteins (total Lowry proteins, 1 mg), is stirred with a mixture of chloroform:methanol:water (4.5:4.5:0.4 v/v/v) at room temperature for 1 hour. The solvent is removed by filtration or by sucking it off with a pipet and 2-3 further extractions are done. The extracts are combined, filtered if necessary and evaporated. The combined evaporated extract is taken up in chloroform:methanol:water (6.5:2.5:0.4 v/v/v) and applied to a thin layer plate.

Chromatography is performed on a glass or acrylamide plate overlaid with 250μ thick Silica Gel G. The samples are spotted on the origin. The plate is placed in a glass tank containing the developing solvent chloroform:methanol:water (6.5:2.5:0.4 v/v/v). The solvent takes 50-60 minutes to travel 15-18 cm. The plate is dried for 5-10 minutes at 50°-55° C.

Detection is done either on separate plates or on one plate provided that the order is (1) iodine vapor, (2) Rhodamine 6G, (3) phosphomolybdic acid. Quantitation is achieved with a spectrodensitometer.

EXAMPLE 2

The procedure of Example 1 is repeated as far as the treatment with iodine vapor except that 5% of the Triton X-100 is tritium labelled (0.0563 mg of $^3H$ at 1 mCi/mg plus 1 g unlabelled Triton X-100 in 20 ml of water). After the chromatographic plate is dried and the spots are visualized with the iodine vapor, the spots are cut out from the plate and their radioactivity counted. From the count results, the amount of residual surfactant in each spot is calculated.

What is claimed is:

1. A chromatographic method for the separation, detection and quantitation of an anionic, nonionic or cationic surfactant alone or in a surfactant-containing protein, glycoprotein, lipoprotein, polysaccharide, or lipopolysaccharide at levels below about 5 μg 1 mg comprising
    extracting the surfactant or surfactant-containing protein, glycoprotein, lipoprotein, polysaccharide, or lipopolysaccharide with a solvent mixture comprising a haloalkane, a water-miscible alkanol and water,
    subjecting the extract containing the surfactant to thin layer chromatography wherein the support medium is a silica or alumina gel and the developing solvent is a mixture comprising a haloalkane, a water-miscible alkanol and water,
    removing the developing solvent, and
    detecting the surfactant sequentially with (a) iodine vapor, (b) rhodamine 6G and (c) phosphomolybdic acid, or with radiolabeled surfactant.

2. A method according to claim 1 wherein the detection is effected sequentially with (a) iodine vapor, (b) rhodamine 6G and (c) phosphomolybdic acid.

3. A method according to claim 1 wherein the detection is effected with radiolabeled surfactant.

4. A method according to claim 1 wherein the rhodamine 6G is employed in alcohol solution.

5. A method according to claim 4 wherein the alcohol is methanol.

6. A method according to claim 1 wherein the phosphomolybdic acid is employed in ethanol/ether.

7. A method according to claim 1 wherein the haloalkane is chloroform.

8. A method according to claim 1 wherein the water-miscible alkanol is methanol.

9. A method according to claim 8 wherein the haloalkane is chloroform.

10. A method according to claim 1 wherein the extracting and developing solvents comprise chloroform, methanol and water.

* * * * *